United States Patent [19]

Schmotzer et al.

[11] Patent Number: 5,755,804
[45] Date of Patent: May 26, 1998

[54] ENDOPROSTHETIC KNEE JOINT

[75] Inventors: Hans Schmotzer, Aarau; Willi Horber, Zurich, both of Switzerland

[73] Assignee: Plus Endoprothetik AG, Rotkreuz, Switzerland

[21] Appl. No.: 804,374

[22] Filed: Feb. 21, 1997

[30] Foreign Application Priority Data

Feb. 21, 1996 [DE] Germany ............... 196 06 461.9
May 7, 1996 [DE] Germany ............... 196 18 321.9

[51] Int. Cl.⁶ ............................................. A61F 2/38
[52] U.S. Cl. ............................................ 623/20
[58] Field of Search ........................... 623/16, 18, 20

[56] References Cited

U.S. PATENT DOCUMENTS

| | | | |
|---|---|---|---|
| 4,136,405 | 1/1979 | Pastrick et al. | 623/20 |
| 4,301,553 | 11/1981 | Noiles | 623/20 |
| 4,462,120 | 7/1984 | Rambert et al. | 623/20 |
| 4,538,306 | 9/1985 | Dörre et al. | 623/20 |
| 4,662,889 | 5/1987 | Zichner et al. | 623/20 |
| 5,139,521 | 8/1992 | Schelhas | 623/20 |
| 5,411,555 | 5/1995 | Nieder | 623/20 |
| 5,413,607 | 5/1995 | Engelbrecht et al. | 623/20 |
| 5,489,311 | 2/1996 | Cipolletti | 623/20 |

*Primary Examiner*—Mary Beth Jones
*Attorney, Agent, or Firm*—Knobbe, Martens, Olson & Bear LLP

[57] ABSTRACT

An endoprosthetic knee joint has a femur portion, a tibia portion, and a coupling portion. The femur portion has a femur shaft having convexly curved condyle shells at a lower end, the shells having primary slide surfaces and two spaced apart side walls forming an intercondylar space. The tibia portion has a tibia shaft with a tibia plateau at an upper end, upon which are formed secondary slide surfaces. The tibia plateau has an axial recess with a cross-section which expands toward the plateau from the depth of the recess on one side to a slot in the plateau. The coupling portion has a coupling pin rotatably housed in the recess, and a joint head at the upper end of the pin projects into the intercondylar space. During coupling of the parts of the prosthesis, the knee need not be stretched by the length of the coupling pin, but rather the pin can be introduced into the tibia portion by simple pivoting.

13 Claims, 2 Drawing Sheets

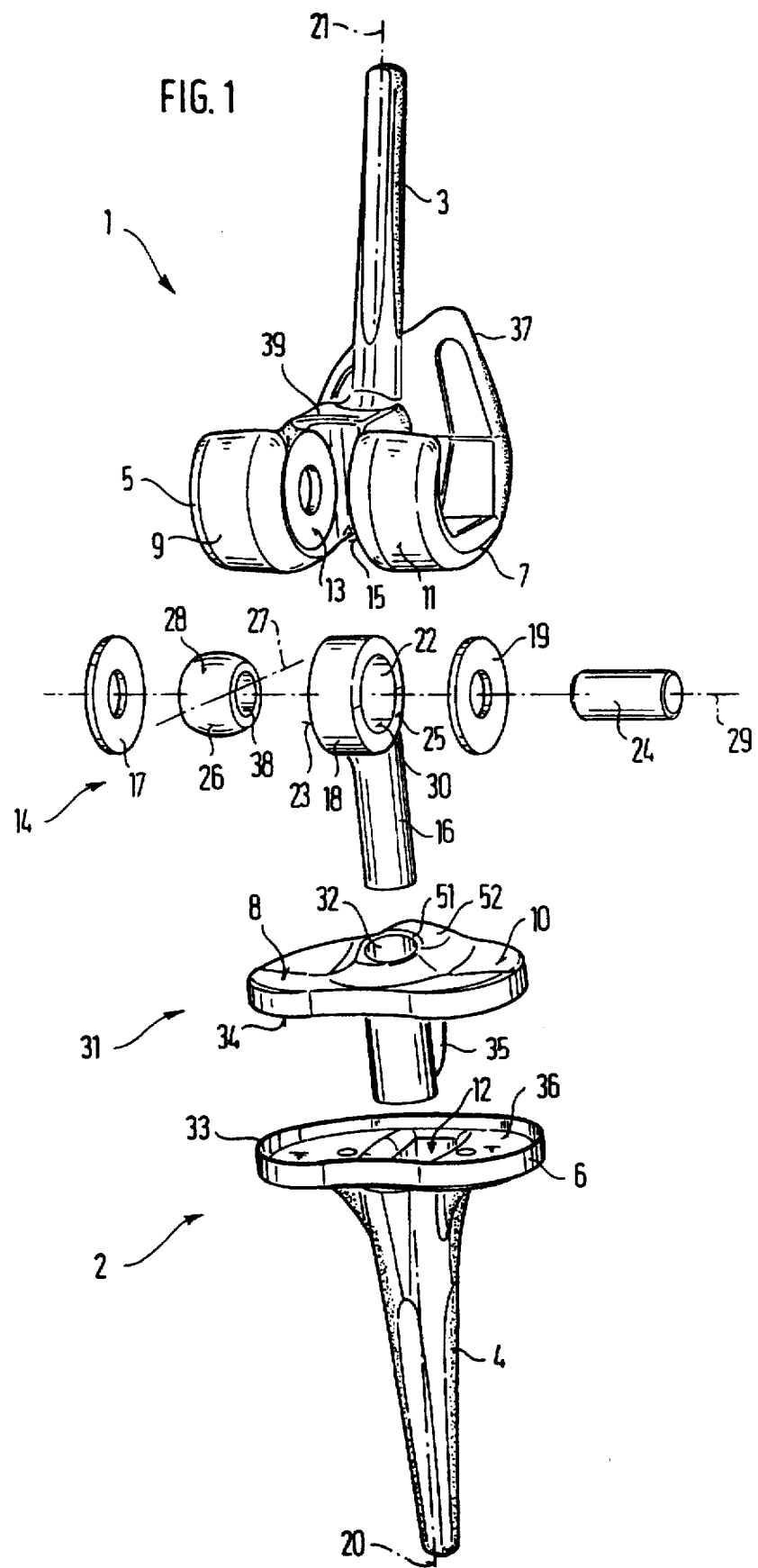

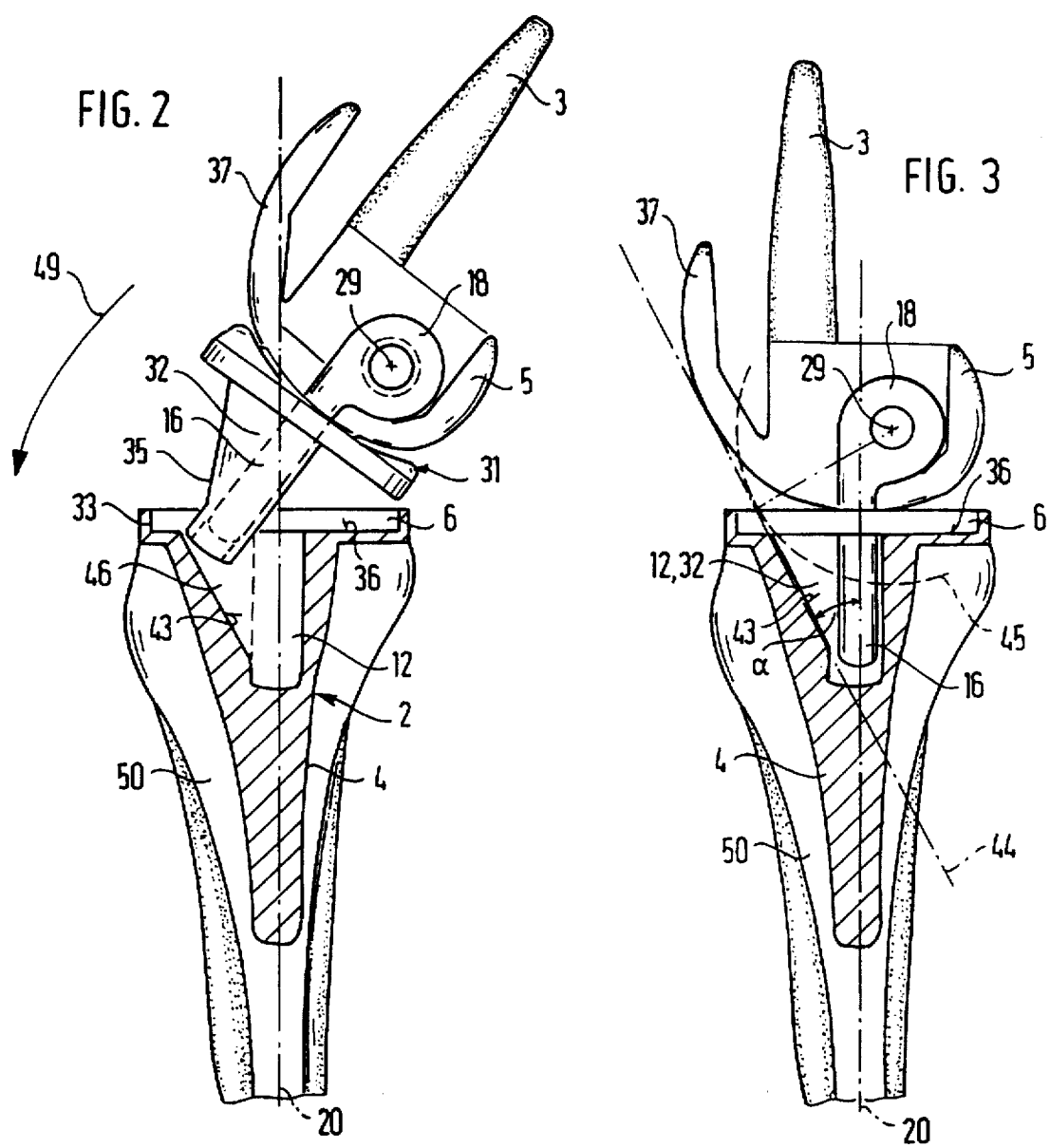
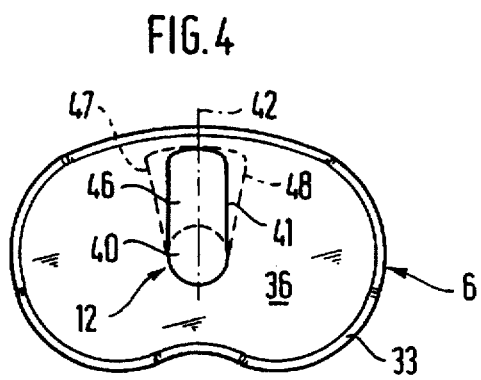

ENDOPROSTHETIC KNEE JOINT

BACKGROUND OF THE INVENTION

The invention relates to an endoprosthetic knee joint with a femur portion having, at the lower end of a femur shaft, convexly curved condylar shells with first sliding surfaces which have dorsally two spaced-apart side walls forming an intercondylar space, with a tibia portion having, at the upper end of a tibia shaft, a tibia plateau upon which there are formed secondary sliding surfaces corresponding to the first sliding surfaces of the condylar shells, and which has an aperture extending axially in the tibia shaft, and with a coupling portion having at the upper end of a coupling pin accommodated rotatably in the aperture, a joint head projecting into the intercondylar space, which is mounted to pivot about a pivotal axis extending transversely to the femur axis.

Endoprosthetic knee joints, which by means of a hinge joint enable the flexion/extension movement between femur and tibia, are generally termed "prosthetic hinges", and their pivotal axis also as "hinge axis". Such a prosthetic hinge is known for example from DE 35 29 894 C2 or from EP 0 174 531. During assembly of the prosthesis, they are no longer coupled to the hinge axis, but to the coupling pin, which is either secured on the tibia and projects upwards and articulates with a ring secured to the hinge joint, or is secured to the hinge joint and is inserted into the recess into the tibia portion. Thus the coupling pin of the coupling portion substantially fulfils three tasks: on the one hand, in addition to the flexion/extension movement of the hinge axis, it enables a rotation about the tibia axis. On the other hand it transmits the anterior/posterior thrust forces from the femur to the tibia. Finally, the coupling pin enables distraction of the knee joint under tension stress, so that the latter is not transmitted to the anchorage of the endoprosthesis.

The problem addressed by the present invention is connected with the third task to be carried out by the coupling pin, namely enabling distraction of the knee joint under tension. Here the problem arises that the possible distraction path, i.e. the necessary length of the coupling pin, must be large enough to avoid dislocation of the component groups of the prosthetic joint even when the ligaments are under massive tension, i.e. extreme distraction. However, the longer the coupling pin the more difficult is non-damaging intraoperative coupling of the parts of the prosthesis, which in many cases will no longer be possible even if the remaining ligament structures of the knee joint are forcibly stretched, distorted or released by cutting.

SUMMARY OF THE INVENTION

The present invention concerns itself with this problem, an object being seen as further to develop an endoprosthetic knee joint of the type already mentioned in such a way that even in the case of a lengthy coupling pin, non-damaging intraoperative coupling of the prosthesis parts is possible in a simple manner.

This object is achieved in the endoprosthetic knee joint in one aspect of the present invention in that the cross-section of the recess in the tibia portion expands towards the tibia plateau from the depth of the recess on one side to a slot in the tibia plateau.

Thus the opening width of the recess for accommodating the coupling pin is enlarged and at the same time displaced, so that a slot diverging in the proximal direction results. The advantages of the solution according to the invention reside particularly in the fact that during coupling of the parts of the prosthesis, the knee need not be stretched by the length of the coupling pin, but that the latter, utilising the additional free space available due to the divergent shape of the recess, can be introduced into the tibia portion by simple pivoting. Thus during assembly of the parts of the prosthesis, considerably less extension of the ligaments is necessary.

Thus it is preferably provided that the longitudinal axis of the elongate slot extends substantially from the posterior to the anterior, while the actual portion of the recess extends substantially parallel or flush with the tibia axis. The increase in the opening cross-section of the recess is thus displaced in the anterior direction, for which reason the femur portion can be inserted in a substantially simplified way from the posterior in an initially oblique configuration.

In order more precisely to align the divergent portion of the recess providing the additional free space, the anterior inner edge of the divergent recess extending from the depth of the recess obliquely upwards in the direction of the tibia plateau, when the prosthesis is assembled, is a tangent to an arc about the pivotal axis of the joint head. Thus the configuration of the inner edge in the longitudinal section of the recess is defined by the apex, extending from the bottom upwards, of the slot, and the angle α between the tangent and the tibia axis is a measure for the inclination of each inner edge. This latter can be optionally rectilinear, concave or convex, or in the form of a combination of at least two of these shapes. In addition, during insertion of the femur portion it can be advantageous if the side walls of the divergent recess optionally likewise diverge towards the tibia plateau, or in the anterior direction, or both in the anterior direction and towards the tibia plateau. Thus the divergence in the anterior direction leads to a trapezoid-like cross-sectional shape opening towards the anterior, the internal shape of the recess being optionally capable of being laterally symmetrical or laterally asymmetrical.

The axial portion of the recess preferably has a greater axial extension than the divergent portion. In this way it is brought about that coupling of the parts of the prosthesis terminates with a unidirectional lowering of the femur portion into the tibia portion.

It is conventional for endoprosthetic knee joints of the type here described to arrange, between the support surface of the tibia plateau and the primary slide surfaces of the condyle shells, an inlay which reduces wear on the prosthesis. Such an inlay has a base surface, two slide surfaces on the upper side and a bore for passage of the coupling pin. In further developments of the present invention it is preferably provided that a sleeve member is set on the base surface of the inlay, the cavity of said sleeve member being flush with the bore of the inlay, and its outer shape being substantially complementary with the inner shape of the recess in the tibia portion. The substantial advantages of such a sleeve member as a component of the inlay reside particularly in handling of the prosthesis and in simplified intraoperative coupling of its components; that is to say, during coupling, the inlay is firstly thrust with the sleeve member on to the coupling pin, and then the coupling pin together with the inlay is introduced into the divergent recess in the tibia portion. As the axial bore of the recess is slightly deeper than the divergent portion, coupling terminates with an axial lowering of the inlay into the tibia portion, effecting a complete positive connection of the inlay with the lateral edge of the support surface of the tibia plateau and of the sleeve member with the recess in the tibia portion. Appropriate securing means such as screws, snap-in devices or similar prevent subsequent dislocation of the intermediate member from the tibia portion.

The coupling sequence for the parts of the prosthesis which can be carried out with the endoprosthetic knee joint according to the invention, namely firstly connection of the inlay with the femur portion or with the coupling portion secured thereon, and thereafter connection of these two parts of the tibia portion, contrasts in an extremely advantageous way with the coupling sequence in known endoprosthetic knee joints, in which firstly the femur portion is coupled to the tibia portion and the inlay is then inserted.

The sleeve member may be integral with the base surface of the inlay or may be designed as a separate component. In its embodiment as a separate component three variants are provided, the first two variants differing from one another in the way in which the sleeve member is separated from the inlay.

In the first variant, an aperture for insertion of the sleeve member should be provided in the inlay, this being effected for instance by four vertical incisions through the inlay. In this case during coupling the inlay would first be combined with the tibia portion and then the coupling pin with the sleeve member first thereon introduced into the divergent recess in the tibia portion. Here also appropriate securing means would prevent subsequent dislocation of sleeve member and inlay. In this embodiment the inlay could also be prefabricated in the workshop, which would further reduce the risk of dislocation.

In a further advantageous development in the first variant as a separate component, the upper edge of the sleeve member, after insertion into the aperture in the inlay, is flush with the upper side of the inlay.

In the second variant of the sleeve member as a separate component, instead of the anterior aperture, a posterior one is provided in the form of a slot. For this purpose the sleeve member is for example separated from the underside of the inlay by a single horizontal cut. During coupling, the coupling pin would firstly be introduced with the thrust-on sleeve member into the divergent recess of the tibia portion, and then the inlay would be pushed on above the sleeve member on to the tibia plateau. In this case the upper edge of the sleeve member after insertion would then preferably be flush in the aperture in the tibia portion with the support surface of the tibia plateau. The advantage of this embodiment resides in the simplified selection of an appropriately thick inlay. In addition, the inlay secures the sleeve member additionally against dislocation. The posterior aperture in the inlay can be bridged over by a filler member previously mounted on the tibia plateau, or can also be left free. This is possible because no important function is ascribed to the posterior central region.

The third variant is a sub-variant to the first and second variants. Here the sleeve member is subdivided along the tibia axis, so that a posterior and an anterior half-shell result. The posterior portion forms an integral component with the said filler member and is previously mounted on the tibia portion. The anterior portion can likewise be formed as a separate component as in the above examples, or can be added to the underside of the inlay. Coupling is then effected in accordance with the embodiments described above.

BRIEF DESCRIPTION OF THE DRAWINGS

A preferred embodiment of the invention, given by way of example, is explained in more detail in the following with reference to a drawing, which shows:

FIG. 1 an exploded view of an endoprosthetic knee joint;

FIG. 2 a ventral-dorsal vertical section through a tibia section, a tibia portion and a femur portion and an inlay during insertion;

FIG. 3 a view corresponding to that in FIG. 2, yet with the femur portion and inlay inserted; and FIG. 4 a schematic plan view of the support surface of a tibia plateau.

DETAILED DESCRIPTION OF THE PREFERRED EMBODIMENTS

FIG. 1 shows an exploded view of an endoprosthetic knee joint, which substantially comprises four component groups: a femur portion 1 with a femur shaft 3 and convexly curved condyle shells 5, 7 located on their lower end, which are extensively adapted to the natural condyles and have on their underside primary slide surfaces 9, 11, and which have dorsally two spaced-apart side walls 13, 15, which are connected by a web to form a box 39 and form within the box 39 an intercondylar space. The two condyle shells 5, 7 merge ventrally into one another and at that point form a patella plate 37 for articulation with the patella.

The pendant to the femur portion 1 is a tibia portion 2 with a tibia shaft 4 and a tibia plateau 6 at its upper end, which has a support surface 36, having a recess 12 extending axially in the tibia shaft 4, and a lateral edge 33 for accommodating a third component group 31.

This third component group 31 comprises an inlay with a base surface 34 for mounting on the support surface 36 of the tibia portion 2, with a sleeve member 35 to be set on the base surface 34 and which, in order to attach the inlay 31 to the tibia portion 2, is thrust into the recess 12 of the tibia portion 2, further with secondary slide surfaces 8, 10 on the upper side of the inlay 31, which are concavely curved in the ventral-dorsal direction, and upon which the condyle shells 5, 7 of the femur portion 1 are supported. In order to attach the fourth component group, the coupling portion 14 on the tibia portion 2, the inlay 31 has a bore 32, which extends through the upper side of the inlay and through the sleeve member 35.

The coupling portion 14 has as a central element a coupling pin 16 and, on its upper end, a joint head 18 projecting into the intercondylar space of the femur portion 1. In the assembled state of the endoprosthetic knee joint, the coupling pin 16 is rotatably accommodated in the bore 32 of the inlay 31 and thus in the recess 12 of the tibia portion 2. The joint head 18 has a bore 22 extending transversely to the tibia axis 20 or transversely to the femur axis 21, and is mounted to pivot about a substantially horizontal joint axis 29 in the side walls 13, 15 of the condyle shells 5, 7. The bore 22 in the joint head 18 has a slide surface 30 which is so shaped that it forms a bearing seat for a slide bush 26, which in the assembled state of the endoprosthetic knee joint is located between the coupling bolt 24 and the joint head 18, i.e. is thrust with its bore 38 on to the coupling bolt 24. In the embodiment shown in FIG. 1, the slide bush has a spherical external peripheral surface 28, which co-operates with the correspondingly-shaped slide surface 30 of the joint head 18 and enables subdivision of the joint surfaces on the cylindrical coupling bolt 24 and the spherical slide bush 28; the cylindrical coupling bolt 24 takes over exclusively the flexion/extension movement between the coupling bolt and the slide bush, while the spherical slide bush 26 takes over both the varus-valgus movement and a rotational movement between slide bush and joint head. The external peripheral surface 28 could naturally also have any other appropriate shape. In order to reduce wear between the side surfaces 23, 25 of the joint head on the one hand and the side walls 13, 15 of the condyle shells 5, 7 rotating against them on the other hand, discs 17, 19 are provided which are likewise thrust on to the coupling bolts 24.

FIG. 2 shows a ventral-dorsal vertical section through an upper tibia section 50, a tibia portion 4 inserted into the tibia section 50 and a femur portion set on for insertion (coupling), with an inlay 31. The coupling portion with the coupling pin 16 and the joint head 18 is suspended by means of the coupling bolt described with reference to FIG. 1 in the intercondylar space and mounted to pivot about a pivotal axis 29. Already thrust on to the coupling pin 16 is the inlay 31 with the sleeve member 35.

With reference to this vertical section through the tibia portion it can be seen that the recess 12, which extends with the first portion axially in the tibia shaft 4, enlarges in a diverging manner from the bottom upwards and in the anterior direction (to the left in the illustration). The anterior inner edge 43 of the recess 12 thus extends from the depth of the recess obliquely in the direction of the tibia plateau 6. The additional free space 46 provided by this divergent formation of the recess 12, which extends substantially from the posterior to the anterior, even in the case of longer coupling pins 16 enables intraoperative insertion of the femur portion 3 and of the inlay 31 without the necessity to over-extend the knee ligament structures or even separate them.

As the axial portion of the recess 12 and the tibia portion 2 is drilled slightly deeper than the divergent portion 46, insertion of the femur portion 3 and of the inlay 31 terminates with an axially-aligned lowering of the inlay into the tibia plateau 6, where a complete positive connection of the inlay 31 with the lateral edge 33 of the support surface 36 of the tibia plateau 6 is achieved. As the sleeve member 35 of the inlay 31 is formed substantially complementary to the internal shape of the diverging recess 12 of the tibia portion 2, insertion also terminates with a complete positive connection of the sleeve member 35 with the recess 12.

FIG. 3 shows the final stage after insertion. It can be seen from this drawing that the oblique anterior inner edge 43 of the recess 12 coincides with a tangent 44 to an arc 45 about the pivotal axis 29 of the joint head 18, which is inclined at an angle α to the tibia axis 20.

FIG. 4 shows a schematic plan view of the tibia plateau 6 and illustrates the configuration of the recess 12. Said recess comprises an axial portion 40 and a divergent portion 46, the divergent portion 46 extending from the axial portion 40 in the anterior direction (upwards in the illustration). In the embodiment shown, the recess 12, in the depth of its extension in the tibia shaft 4, has a substantially circularly symmetrical cross-sectional shape which develops in the direction of the tibia plateau 6 into the cross-sectional shape of an elongate slot 41. Naturally, other cross-sectional shapes of the lower portion of the recess 12 may be imagined, e.g. square, polygonal, oval or rectangular. If necessary it can be advantageous to form the side walls 47, 48 of the recess 12 as likewise diverging from the bottom upwards, as shown in dotted lines in FIG. 4, and both in the anterior direction and towards the tibia plateau, so that a trapezoid-like cross-sectional shape of the recess 12 results.

The non-damaging coupling of the portions of the prosthesis achievable by means of the endoprosthetic knee joint described provides that firstly the inlay 31 is connected with the femur portion 3 by being thrust on to the coupling pin 16, and thereafter the two components are inserted into the tibia portion 2 by the oblique projection shown in FIG. 2.

What is claimed is:

1. An endoprosthetic knee joint, comprising:

a femur portion having at a lower end of a femur shaft convexly curved condyle shells with primary slide surfaces, said shells having two spaced-apart side walls forming an intercondylar space;

a tibia portion having at an upper end of a tibia shaft a tibia plateau on which there are formed secondary slide surfaces corresponding to the primary slide surfaces of the condyle shells, said tibia plateau having a recess extending axially in the tibia shaft; and a coupling portion having a coupling pin rotarily housed in said recess, an upper end of said coupling pin having a joint head projecting into said intercondylar space, said joint head being mounted to pivot about a pivotal axis extending transversely to the femur axis, a cross-section of the recess of the tibia portion enlarging towards the tibia plateau from the depth of the recess on one side to an elongate slot in the tibia plateau.

2. An endoprosthetic knee joint according to claim 1, wherein a longitudinal axis of the elongate slot extends substantially from the posterior to the anterior.

3. An endoprosthetic knee joint according to claim 1, wherein an anterior inner edge extending from the depth of the recess obliquely in the direction of the tibia plateau of the recess, when said endoprosthetic knee joint is assembled, is a tangent to an arc about the pivotal axis of the joint head.

4. An endoprosthetic knee joint according to claim 1, wherein an oblique inner edge of the recess is rectilinear, concave or convex, or in the form of a combination of at least two of these shapes.

5. An endoprosthetic knee joint according to claim 1, wherein side walls of the recess diverge towards the anterior and/or towards the tibia plateau.

6. An endoprosthetic knee joint according to claim 1, wherein an axial portion of the recess has a greater axial extension than a divergent portion.

7. An endoprosthetic knee joint according to claim 6, wherein the axial extension comes to at least the height of a lateral rim defining a support surface of the tibia plateau.

8. An endoprosthetic knee joint according to claim 1, further comprising an inlay located between a support surface of the tibia plateau and the primary slide surfaces of the condyle shells, the inlay having a base surface, secondary slide surfaces on an upper side, and a bore for the introduction of the coupling pin, a sleeve member set on the base surface having a cavity flush with the bore.

9. An endoprosthetic knee joint according to claim 8, wherein the sleeve member is substantially complementary to the internal shape of the recess of the tibia portion.

10. An endoprosthetic knee joint according to claim 8, wherein the sleeve member is a separate component, and there is provided in the inlay an aperture for insertion of the sleeve member.

11. An endoprosthetic knee joint according to claim 10, wherein an upper edge of the sleeve member, after insertion into the aperture in the inlay, is flush with the upper side of the inlay.

12. An endoprosthetic knee joint according to claim 8, wherein the sleeve member is a separate component, and an upper edge of the sleeve member, after insertion into the recess in the tibia portion, is flush with the support surface of the tibia plateau.

13. An endoprosthetic knee joint according to claim 8, wherein the sleeve member is subdivided along the tibia axis so that a posterior and an anterior half shell result.

* * * * *